United States Patent
Goodson, Jr. et al.

(10) Patent No.: US 6,353,128 B1
(45) Date of Patent: *Mar. 5, 2002

(54) PHENYL ACETAMIDES AS SPLA₂ INHIBITORS

(75) Inventors: Theodore Goodson, Jr.; Richard Waltz Harper; David Kent Herron, all of Indianapolis, IN (US)

(73) Assignee: Eli Lilly and Company, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/976,858

(22) Filed: Nov. 24, 1997

Related U.S. Application Data

(60) Provisional application No. 60/032,508, filed on Dec. 3, 1996.

(51) Int. Cl.⁷ ............................................. C07C 229/00
(52) U.S. Cl. .............................. 560/41; 560/39; 562/41; 562/51; 558/49; 558/173; 514/534; 514/568; 514/617
(58) Field of Search ....................... 560/39, 41; 562/41, 562/51; 558/49, 173; 514/534, 568, 617

(56) References Cited

U.S. PATENT DOCUMENTS 4,256,758 A * 3/1981 Cragio, Jr. et al. ......... 424/274

FOREIGN PATENT DOCUMENTS

| | | | |
|---|---|---|---|
| EP | 0021 228 A1 | 1/1981 | ................. 207/456 |
| EP | 161529 A2 | 11/1985 | |
| EP | 0021 228 A1 | 1/1988 | ................. 207/456 |
| EP | 0338 306 A2 | 10/1989 | ................... 69/734 |
| EP | 0779 271 A1 | 6/1997 | ................... 233/11 |
| GB | 1 584 246 A | 2/1981 | |

OTHER PUBLICATIONS

Takahashi et al., *Chemical Abstracts*, AN 105:29537, 10(4), pp. 629–642, (1985).
Takashi, et al., "Photodegradation of the Pyrethroid Insecticide Fenpropathrin in Water, on Soil and on Plant Foliage", *Pestic. Sci.*, 16, pp. 119–131, (1985).
Rooney, et al., "Inhibitors of Glycolic Acid Oxidase", *J. Med. Chem.*, 26(5), pp. 700–714, (1986).
Chemical Abstracts AN CA53:7073g 1996.
DE 371,8638 A1 Dec. 22, 1988.
Andre M., et al., Identification of the thermal degradation products of G–triiodothyronine sodium (liothyronine sodium) by reversed–phase high–performance liquid chromatogrpahy with photogiode–array UV and mass spectrometic detection, Journal of Chromatography A, 725 (1996) 287–294.

\* cited by examiner

*Primary Examiner*—Paul J. Killos
(74) *Attorney, Agent, or Firm*—Francis O. Ginah; Arleen Palmberg

(57) ABSTRACT

A class of novel phenyl acetamides is disclosed together with the use of such compounds for inhibiting sPLA₂ mediated release of fatty acids for treatment of conditions such as septic shock.

12 Claims, No Drawings

PHENYL ACETAMIDES AS SPLA$_2$ INHIBITORS

This application claims the benefit of U.S. Provisional No. 60/032,508, filed Dec. 3, 1996.

BACKGROUND OF THE INVENTION

This invention relates to novel substituted phenyl acetamides useful for inhibiting sPLA$_2$ mediated release of fatty acids for conditions such as septic shock.

The structure and physical properties of human non-pancreatic secretory phospholipase A$_2$ (hereinafter called, "sPLA$_2$") has been thoroughly described in two articles, namely, "Cloning and Recombinant Expression of Phospholipase A$_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; The Journal of Biological Chemistry, Vol. 264, No. 10, Issue of Apr. 5, pp. 5335–5338, 1989; and "Structure and Properties of a Human Non-pancreatic Phospholipase A$_2$" by Kramer, Ruth M.; Hession, Catherine; Johansen, Berit; Hayes, Gretchen; McGray, Paula; Chow, E. Pingchang; Tizard, Richard; and Pepinsky, R. Blake; The Journal of Bioloaical Chemistry, Vol. 264, No. 10, Issue of Apr. 5, pp. 5768–5775, 1989; the disclosures of which are incorporated herein by reference.

It is believed that sPLA$_2$ is a rate limiting enzyme in the arachidonic acid cascade which hydrolyzes membrane phospholipids. Thus, it is important to develop compounds which inhibit sPLA$_2$ mediated release of fatty acids (e.g., arachidonic acid). Such compounds would be of value in general treatment of conditions induced and/or maintained by overproduction of sPLA$_2$; such as septic shock, adult respiratory distress syndrome, pancreatitis, trauma-induced shock, bronchial asthma, allergic rhinitis, rheumatoid arthritis, and etc.

It is desirable to develop new compounds and treatments for sPLA$_2$ induced diseases.

This invention provides compounds known as phenyl acetamides of the formula I

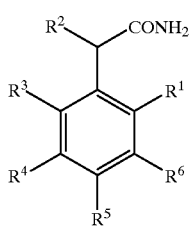

(I)

wherein:

$R^1$ is —H or —O(CH2)$_n$Z;

$R^2$ is —H or —OH;

$R^3$ and $R^4$ are each independently —H, halo or —(C$_1$–C$_4$) alkyl;

One of $R^5$ and $R^6$ is —YR$^7$ and the other is —H, where Y is —O— or —CH$_2$— and R$^7$ is phenyl or phenyl substituted with one or two substituents selected from the group consisting of halo, —(C$_{1-C4}$)alkyl, (C$_1$–C$_4$) alkoxy, phenyl or phenyl substituted with one or two halo groups;

Z is —CO$_2$R, —PO$_3$R$_2$ or —SO$_3$R where R is —H or —(C$_1$–C$_4$)alkyl; and n is 1–8;

or a pharmaceutically acceptable salt, racemate or optical isomer thereof;

provided that when R$^6$ is YR$_7$, R$^1$ is hydrogen; and
when R$^1$, R$^2$, R$^3$, R$^4$ and R$^6$ are hydrogen and R$^5$ is YR$^7$ where Y is —O—, R$^7$ cannot be phenyl; and
when R$^1$, R$^2$, R$^3$, R$^4$ and R$^6$ are hydrogen and R$^5$ is YR$^7$ where Y is CH$_2$, R$^7$ cannot be phenyl substituted with one methoxy or two chloro groups.

This invention is also a pharmaceutical formulation comprising a compound of formula I in association with one or more pharmaceutically acceptable diluents, carriers and excipients.

This invention is also a method of inhibiting sPLA$_2$ comprising administering to a mammal in need of such treatment a therapeutically effective amount of a compound of formula II.

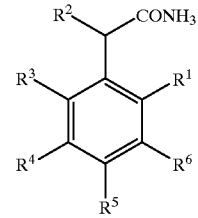

(II)

wherein:

$R^1$ is —H or —O(CH$_2$)$_n$Z;

$R^2$ is —H or —OH;

$R^3$ and $R^4$ are each independently —H, halo or —(C$_{1-C4}$) alkyl;

one of $R^5$ and $R^6$ is —YR$^7$ and the other is —H, where Y is —O— or —CH$_2$— and R$^7$ is phenyl or phenyl substituted with one or two substituents selected from the group consisting of halo, —(C$_{1-C4}$)alkyl, (C$_1$–C$_4$) alkoxy, phenyl or phenyl substituted with one or two halo groups;

Z is —CO$_2$R, —PO$_3$R$_2$ or —SO$_3$R where R is —H or —(C$_{1-C4}$)alkyl; and n is 1 to 8;

or a pharmaceutically acceptable salt, racemate or optical isomer thereof.

According to a further aspect of the present invention, there is provided a method of inhibiting SPLA$_2$ in a mammal in need of such treatment comprising administering to said mammal a therapeutically effective amount of a compound of formula (II).

According to a further aspect of the present invention, there is provided a method of selectively inhibiting sPLA$_2$ in a mammal in need of such treatment comprising administering to said mammal a therapeutically effective amount of a compound of formula (II).

This invention also provides a method of alleviating the pathological effects of septic shock, adult respiratory distress syndrome, pancreatitis, trauma-induced shock, bronchial asthma, allergic rhinitis, rheumatoid arthritis, and related diseases which comprises administering to a mammal in need of such treatment a therapeutically effective amount of the compound of formula II in an amount sufficient to inhibit sPLA$_2$ mediated release of fatty acid and to thereby inhibit or prevent the arachidonic and cascade and its deleterious products.

Other objects, features and advantages of the resent invention will become apparent from the subsequent description and the appended claims.

Definitions:

As used herein, the term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl and the like.

The term "halo" means chloro, fluoro, bromo or iodo.

The term "$(C_1-C_4)$ alkoxy", as used herein, denotes a straight or branched alkyl chain having one to four carbon atoms attached to the remainder of the molecule by an oxygen atom. Typical $C_1-C_4$ alkoxy groups include methoxy, ethoxy, n-propoxy, isopropoxy, n-butoxy, t-butoxy and the like.

The salts of the above phenyl acetamides are an additional aspect of the invention. In those instances where the compounds of the invention possess acidic functional groups various salts may be formed which are more water soluble and physiologically suitable than the parent compound. Representative pharmaceutically acceptable salts include but are not limited to the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "pharmaceutical Salts," *J. Phar. Sci.*, 66: 1–19 (1977)).

Examples of pharmaceutically acceptable organic bases which may be used to prepare pharmaceutically acceptable salts include ammonia, amines such as triethanolamine, triethylamine, ethylamine, and the like. Examples of pharmaceutically acceptable alkali metal bases include compounds of the general formula $MOR^{12}$, where M represents an alkali metal atom, e.g. sodium, potassium, or lithium, and $R^{12}$ represents hydrogen or $C_1-C_6$ alkyl.

The term "acid protecting group" is used herein as it is frequently used in synthetic organic chemistry, to refer to a group which will prevent an acid group from participating in a reaction carried out on some other functional group of the molecule, but which can be removed when it is desired to do so. Such groups are discussed by T. W. Greene in chapter 5 of *Protective Groups in Organic Synthesis*, John Wiley and Sons, New York, 1981, incorporated herein by reference in its entirety.

Examples of acid protecting groups includes esters and substituted esters such as methyl, methoxymethyl, methylthiomethyl, tetrahydropyranyl, methoxyethoxymethyl, benzyloxymethyl, phenylaryl, ethyl, 2,2,2-trichloroethyl, 2-methylthioethyl, t-butyl, cyclopentyl, triphenylmethyl, p-bromobenzyl and trimethylsilyl. A preferred acid-protecting group is methyl.

Certain compounds of the invention may possess one or more chiral centers and may thus exist in optically active forms. For example, compounds where $R^2$ is —OH have a chiral center and form a racemate. The R— and S— isomers and mixtures thereof, including racemic mixtures are contemplated by this invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods.

Preferred Compounds of the Invention

Preferred groups include the following:
(a) $R^1$ is —H;
(b) $R^1$ is —O(CH$_2$)$_n$Z
(c) $R^2$ is —H;
(d) $R^2$ is —OH;
(e) $R^3$ and $R^4$ are each —H;
(f) $R^6$ is —YR$^7$ and $R^7$ is phenyl or phenyl substituted with one or two substituents selected from the group consisting of halo, —($C_{1-C4}$)alkyl, ($C_{1-C4}$)alkoxy, phenyl or phenyl substituted with halo;
(g) $R^5$ is —YR$^7$ where Y is —O— or —CH$_2$— and $R^7$ is phenyl or phenyl substituted with one or two substituents selected from the group consisting of halo, —($C_1-C_4$)alkyl, ($C_1-C_4$)alkoxy, phenyl or phenyl substituted with halo;
(h) $R^7$ is phenyl substituted at the meta positions with one or two substituents selected from the group consisting of halo, —($C_{1-C4}$)alkyl, ($C_1-C_4$)alkoxy, —CF$_3$, phenyl or phenyl substituted at the para position with halo;
(i) $R^7$ is phenyl substituted at the ortho positions with one or two substituents selected from the group consisting of halo, —($C_{1-C4}$)alkyl, ($C_{1-C4}$)alkoxy, —CF$_3$, phenyl or phenyl substituted at the para position with halo;
(j) $R^7$ is phenyl or phenyl substituted with halo;
(k) Z is —CO$_2$H, —PO$_3$H$_2$ or —SO$_3$H; and
(l) n is 4–5.

Further typical examples of compounds of formula I which are useful in the present invention include:

4-(2,6-difluorophenoxy)-5-ethylphenylacetamide;
4-(3-ethoxyphenoxy)-6-chlorophenylacetamide;
4-(5-isopropylphenoxy)-5,6-dichlorophenylacetamide;
3-(4-methylphenoxy)-phenylacetamide;
4-(3,5-diphenylphenoxy)-5-bromophenylacetamide;
4-(4-(3,5-difluorophenyl)phenoxy)-6-methylphenylacetamide;
3-((3-propoxy-5-t-butyl)phenoxy)-phenylacetamide;
3-(2,6-di(4-fluorophenyl)phenoxy)-5,6-dimethylphenylacetamide;
4-(3,5-di-t-butylphenoxy)-5-butylphenylacetamide;
3-(4-(2-bromophenyl)phenoxy)-6-ethylphenylacetamide;
4-(5-chlorophenoxy)-5-propylphenylacetamide;
3-(2-chloro-6-ethoxyphenoxy)-5-chlorophenylacetamide;
4-(2,6-dimethyl)benzyl-5-butylphenylacetamide;
3-(3-propoxy)benzyl-6-ethylphenylacetamide;
3-(5-phenyl)benzyl-5,6(di-t-butyl)phenylacetamide;
3-(4-ethyl)benzylphenylacetamide;
4-(3,5-diphenyl)benzyl-5-chlorophenylacetamide;
3-(4-(3,5-di(4-fluorophenyl)))benzyl-6-butylphenylacetamide;
4-(3-methoxy-5-isopropyl)benzylphenylacetamide;
3-(2,6-diphenyl)benzyl-5,6-dibutylphenylacetamide;
3-(3,5-dimethyl)benzyl-5-fluorophenylacetamide;
4-(4-ethyl)benzyl-5-butylphenylacetamide;
3-(5-bromo)benzyl-5-ethylphenylacetamide;

4-(2,6-diphenyl)benzyl-5,6-dimethylphenylacetamide;
4-(2-methyl-6-methoxy)benzyl-6-fluorophenylacetamid;
2-(3-carboxyprop-1-yloxy)-4-(4-phenylphenoxy) phenyl-2-hydroxyacetamide;
2-(2-carboxyethoxy)-4-(2,6-di(3-chlorophenyl)phenoxy)phenyl-2-hydroxyacetamide;
2-[2-(carboxymethoxy)-4-(3,5-dimethoxyphenoxy)-5-methyl]phenyl-2-hydroxyacetamide;
2-[2-(5-carboxypent-1-yloxy)-4-(phenoxy)-6-hlorolphenyl-2-hydroxyacetamide;
2-[2-(8-carboxyoct-1-yloxy)-4-(2, 6-dimethylphenoxy)-5-fluoro]phenyl-2-hydroxyacetamide;
2-[2-(2-phosophonyl)ethoxy-4-(4-propoxyphenoxy)-6-isopropyl]phenyl-2-hydroxyacetamide;
2-((3-dimethoxyphosphonoly)prop-1-yloxy)-4-(3,5 diethoxy)benzyl-6-ethylphenylacetamide;
2-[2-(diethoxyphosphonoyl)methoxy)-4-phenoxy]phenyl-2-hydroxyacetamide;
2-[2-((8-methoxycarbonyl)oct-1-yloxy)-4-(3-phenylbenzyl)-6-butyl]phenyl-2-hydroxyacetamide;
2-[2-(methoxysulfonyl)methoxy-4-(4-(3,5-di(4-fluorophenyl)phenoxy)-5-ethyl)phenyl-2-hydroxyacetamide;
2-[2-(4-sulfonyl)but-1-yloxy)-4-(4-methoxyphenoxy)-6-fluoro]phenyl-2-hydroxyacetamide;
2-[2-(3-carbomethoxy)prop-1-yloxy)-4-(2, 6-difluorophenoxy)-5-ethyl]phenyl-2-hydroxyacetamide;
2-[2-(2-ethoxycarbonyl)ethoxy-4-benzyl]phenyl-2-hydroxyacetamide;
2-[2-((3-propoxycarbonyl)prop-1-yloxy)-4-(4-(4-chlorophenyl)benzyl)]phenyl-2-hydroxyacetamide;
2-[2-(6-diethoxyphosphonyl)hex-1-yloxy)-4-(3-ethyl-5-methoxyphenoxy)]phenyl-2-hydroxyacetamide;
2-[2-(7-methoxysulfonyl)hept-1-yloxy)-4-((2-fluoro-6-phenyl)benzyl)]phenyl-2-hydroxyacetamide;
2-[2-(3-carboxyprop-1-yloxy)-4-(3-phenylphenoxy)]phenyl-2-hydroxyacetamide:
2-(2-phosphonyl)ethoxy-4-(3-propoxyphenoxy)-5-propylphenylacetamide;
2-((4-diethoxyphosphonyl)but-1-yloxy)-4-(5-t-butylphenoxy)-6-ethylphenylacetamide;
2-(6-phosphonyl)hex-1-yl)-4-(2, 6-dimethylphenoxy)phenylacetamide;
2-((3-diethoxyphosphonyl)prop-1-yloxy)-4-(3-fluoro-5-ethoxybenzyl)-6-methylphenylacetamide;
2-(methoxysulfonyl)methoxy-4-(4-(4-fluorophenyl)benzyl)-6-ethylphenylacetamide;
2-((4-ethoxycarbonyl)but-1-yloxy)-4-benzylphenylacetamide;
2-(2-ethoxycarbonyl)ethoxy-4-(3, 5-diphenylphenoxy)phenylacetamide;
2-(4-(propoxycarbonyl)but-1-yloxy)-4-(4-butoxyphenoxy)phenylacetamide;
2-(8-methoxycarbonyl)oct-1-yloxy)-4-(3-bromo-5-methylbenzyl)-5-propylphenylacetamide;
2-(4-carboxybutoxy)-4-(3-phenylphenoxy)phenylacetamide;

Compounds of formula I where $R^1$ and $R^2$ are H, $R^5$ or $R^6$ are $YR^7$ where $R^7$ is phenyl or substituted phenyl and Y is oxygen can be prepared as illustrated in Scheme I(a), below.

Synthesis Methods

Scheme I (a)

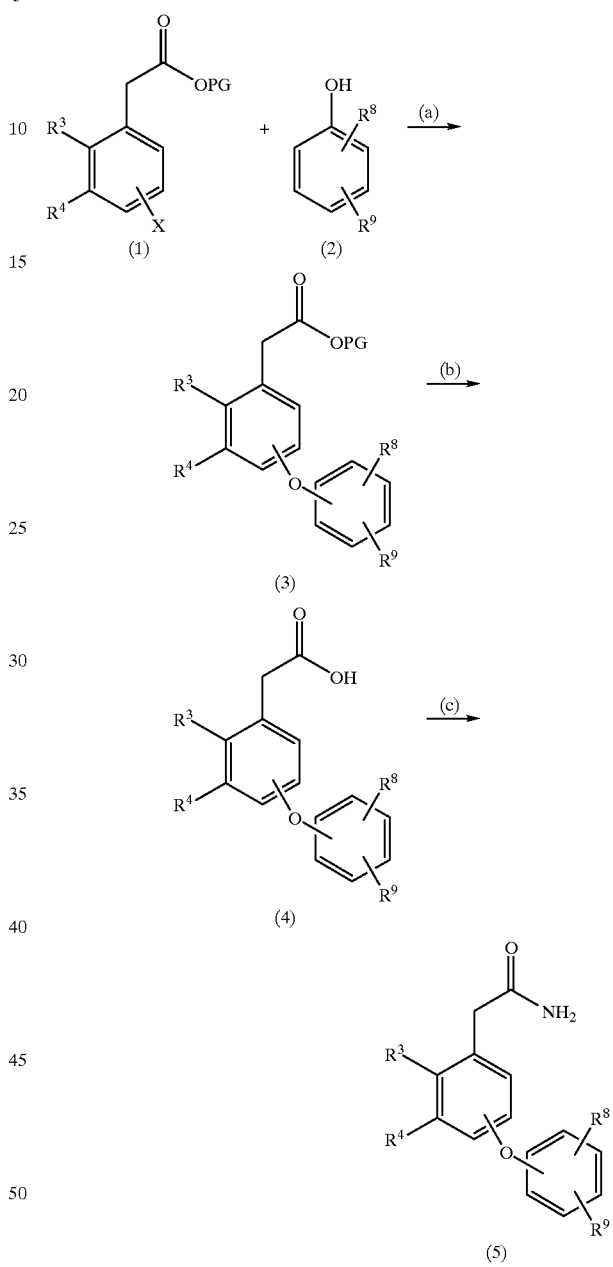

X is halo;
$R^8$ and $R^9$ are each independently —H, halo, —$(C_{1-C4})$ alkyl, $(C_f-C_4)$alkoxy,
phenyl or phenyl substituted with one or two halo groups; and PG is a carboxyl protecting group An appropriately substituted carboxy-protected halophenyl compound (1), where the halogen is preferably bromine, is coupled with an appropriately substituted phenol (2) under modified Ullmann conditions, by refluxing with potassium carbonate and cupric oxide in an aprotic polar solvent, such as pyridine, under an inert gas such as argon. The reaction is substantially complete in 1–24 hours.

Intermediate (3) is deprotected by treatment with a base such as aqueous potassium hydroxide using a solvent, such as diethylene glycol. The reaction, preferably conducted at about 100°–150° C., is substantially complete in 1–24 hours.

Conversion to the amide (5) can then be readily achieved by treatment first with oxalyl chloride in an alkyl halide solvent, such as methylene chloride, using dimethylformamide as a catalyst, at temperatures of from about 0° C. to ambient temperature, followed by treatment with an excess of ammonia gas, again in an alkyl halide solvent.

Alternately, compounds of formula I can be prepared according to the procedure of Scheme I(b), below.

The substituted phenol (2) is coupled with an appropriately substituted benzyl halide (6) as described in Scheme I(a), step a, above, to prepare (7).

Halogenation of (7) is achieved using a halogenating agent, such as N-bromosuccinimide and a catalyst, such as 2,2'azobisisobutyronitrile, in an alkyl halide solvent, such as chloroform, to prepare (8).

Treatment of (8) with sodium cyanide in an aprotic polar solvent, such as dimethyl formamide produces the nitrile (9) which can then be readily converted to the amide (10) by treatment with an aqueous acid, such as hydrochloric acid.

Scheme I (b)

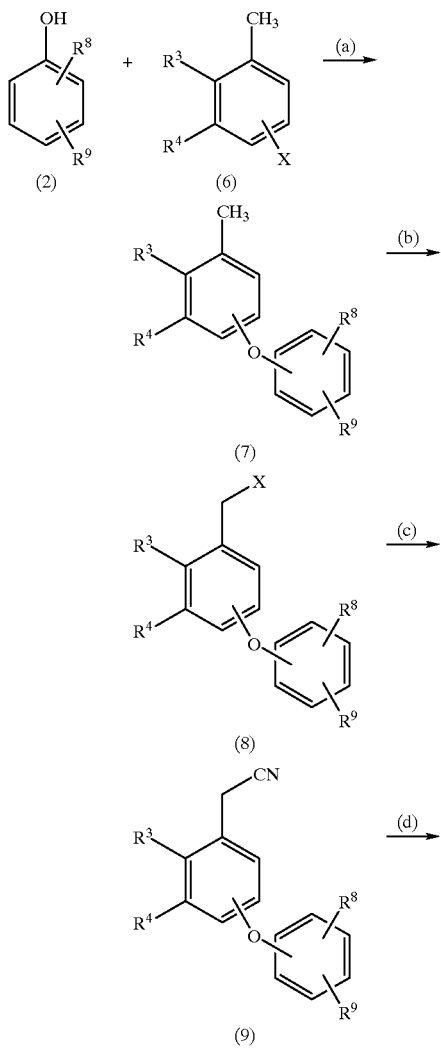

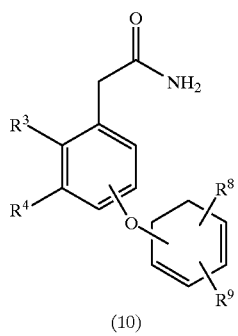

$R^8$ and $R^9$ are as shown Shceme I(a), x is halo.

In another procedure, compounds of formula I where $R^1, R^2, R^3$, and $R^4$ are hydrogen, Y is —O— or —CH$_2$— and $R^7$ is phenyl can be prepared as portrayed in Scheme II on the following page.

Scheme II

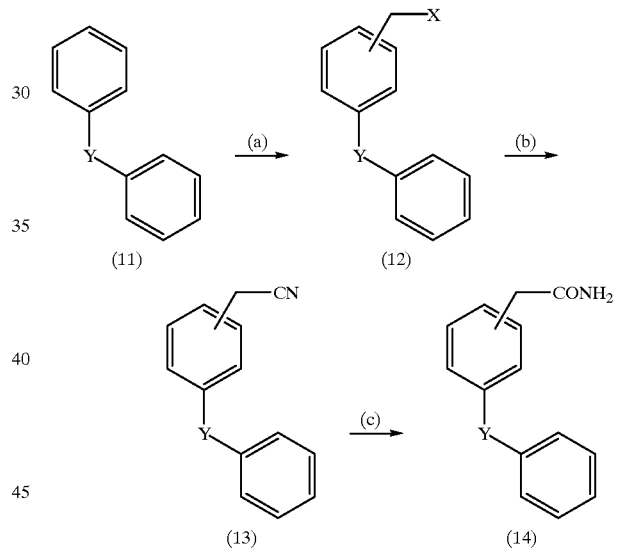

X is a halogen.

An appropriate diphenyl compound (11) is treated with paraformaldehyde and a halogenating agent, such as 40% hydrogen bromide in acetic acid. Two positional isomers result with the X substituent at either the meta or para position of the phenyl ring to which it is attached.

Displacement of the halogen to prepare the nitrile isomers (13) can be achieved by treatment of (12) with sodium cyanide in dimethylformamide as described in Scheme I(b), step (c), above. The isomers can then be readily separated by conventional chromatographic techniques and each isomer may be converted to its respective amide (14) by treatment with hydrogen peroxide and potassium carbonate in an aprotic polar solvent, such as dimethylsulfoxide.

Compounds where $R^1$ is —O(CH$_2$)$_n$Z can be prepared as illustrated in Scheme III, below.

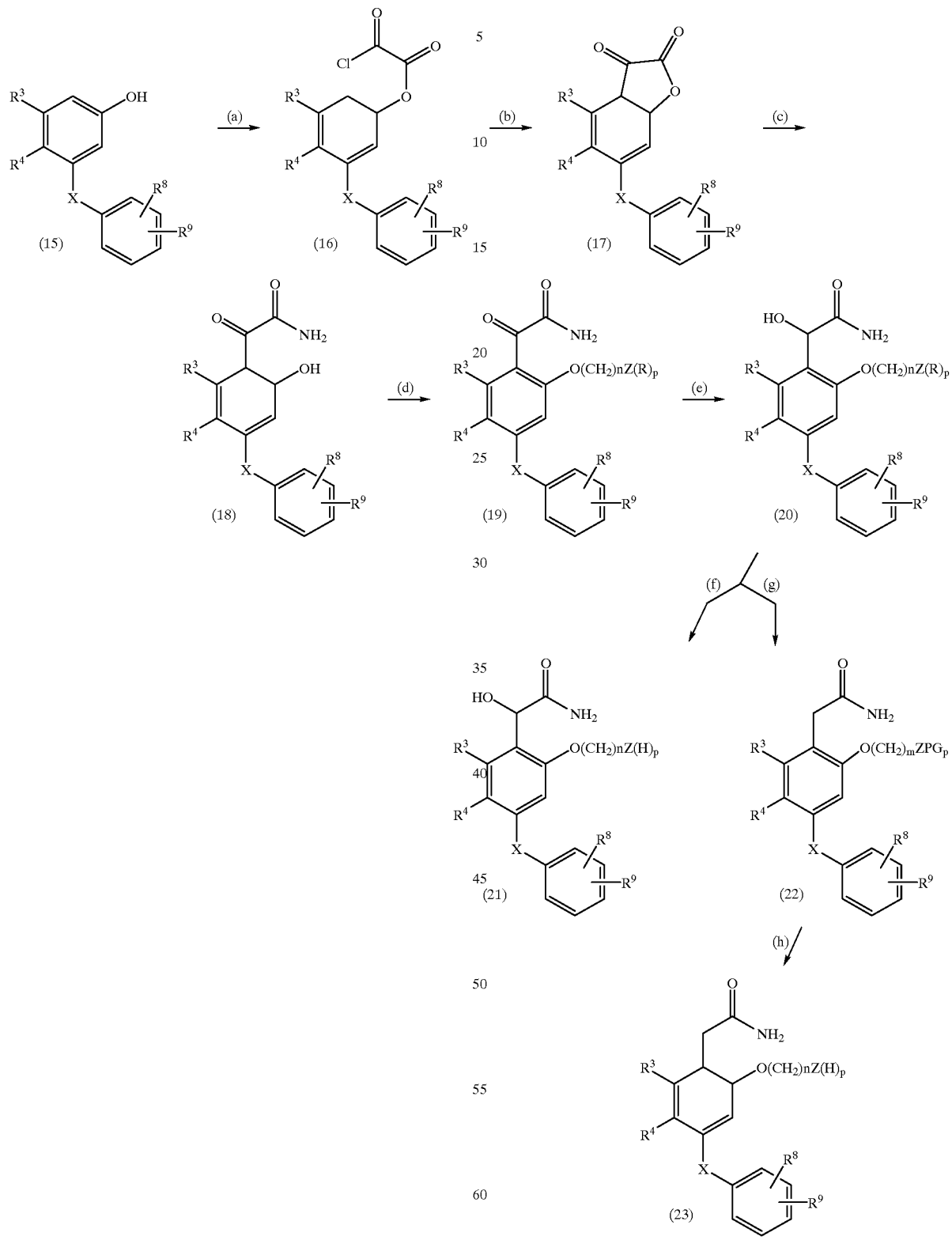

R is —($C_1$–$C_4$)alkyl and p=1 or 2.

Intermediate (16) is prepared by refluxing an appropriately substituted diphenyl compound (15) with oxalyl chloride in an alkyl halide solvent, such as chloroform. Preferably the reaction is catalyzed with 4,4-N-dimethylaminopyridine.

Cyclization to the lactone (17) can be achieved under Friedel-Crafts conditions using a suitable metal halide, such as aluminum chloride, as the catalyst.

Conversion to the glyoxamide (18) can be achieved by aminolysis of the lactone ring using concentrated ammonium hydroxide.

Alkylation of the hydroxy group to prepare the desired alkyl-linked ester (19) occurs by treatment of (18) with an appropriate alkylating agent, such as (X) ($CH_2$)nB where B is $CO_2$PG, —$PO_3$PG or —$SO_3$PG, X is halo and PG is an acid protecting group, preferably methyl.

Partial reduction of the carbonyl in the glyoxamide (19) is achieved by treatment with a suitable reducing agent, such as sodium borohydride in methanol, preferably at temperatures of from 0°–20° C., to prepare the intermediate (20). The desired acid or acid salt (21) can be accomplished by treatment with a suitable base, such as sodium hydroxide.

Further reduction of intermediate (20) can be achieved by treatment with triethylsilane in a strong acid, such as trifluroacetic acid, under an inert gas, such as argon, to prepare (22) followed, again, by conversion to the acid or salt (23) with a strong base.

It will be readily appreciated by the skilled artisan that the starting materials are either commercially available or can be readily prepared by known techniques from commercially available starting materials. For example, when X is oxygen, starting material (15) can be readily prepared by coupling an appropriately substituted phenol with an appropriately substituted phenylhalide to prepare the anisole, under Ullmann-type conditions, by refluxing in the presence of an excess of potassium carbonate and cupric oxide in an aprotic polar solvent such as pyridine. The reaction is preferably conducted under a argon blanket and is substantially complete in from 1 to 48 hours.

Compounds of formula I where Y is —$CH_2$— can be prepared as shown in Scheme IV.

Scheme IV

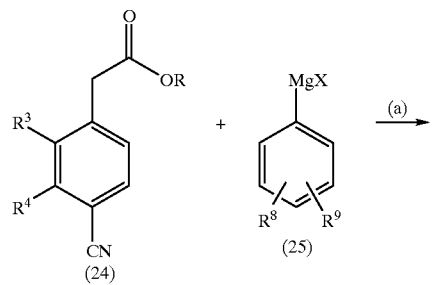

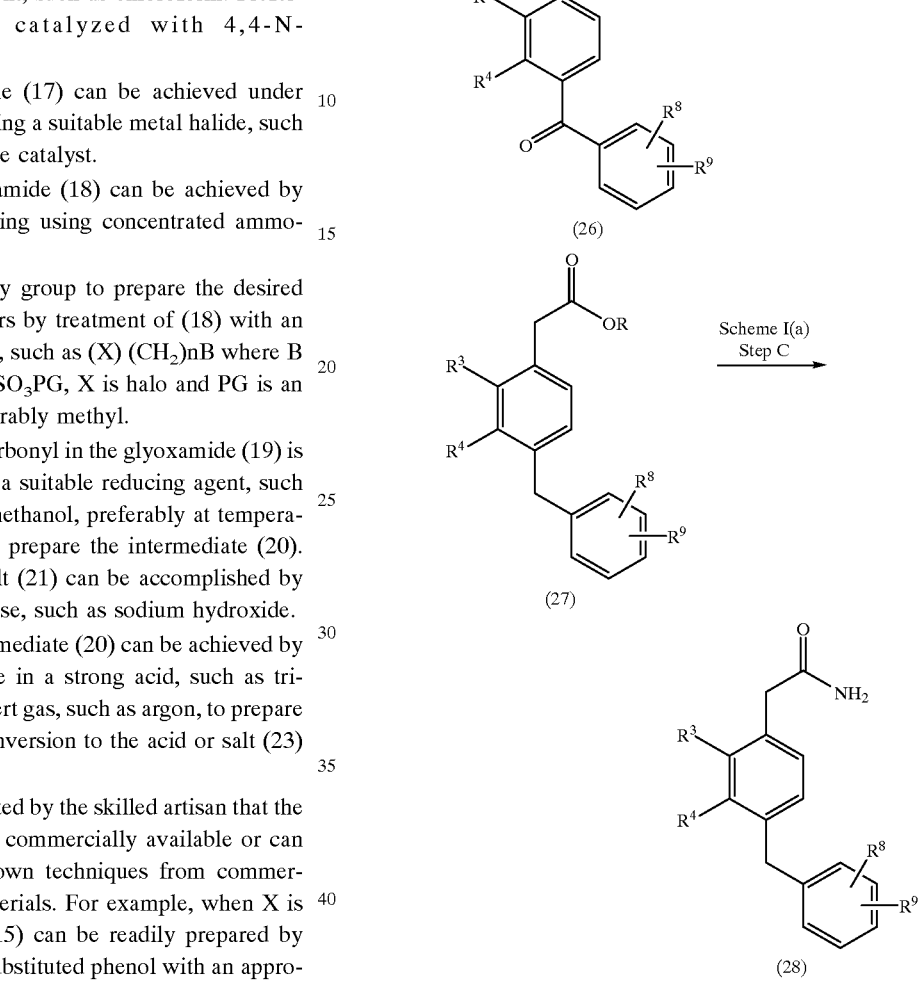

X is a halogen

Using an appropriately substituted phenyl halide, a Grignard reagent (25) is prepared. The phenyl Grignard (25) is then coupled with nitrile (24) and the resultant compound is hydrolyzed with a dilute acid, such as hydrochloric acid to form the intermediate (26).

Reduction of the carbonyl in (26) is accomplished by treatment with a suitable reducing agent, such as sodium borohydride to prepare (27). The reaction is preferably conducted in a solvent catalyst, such as trifluroacetic acid.

The desired acetamide (28) may then be accomplished according to the procedures outlined in Scheme I(a), step (c).

The intermediates and final products may be isolated and purified by conventional techniques, for example by concentration of the solvents, followed by washing of the residue with water, then purification by conventional techniques such as chromatography or recrystallization.

It will be readily appreciated by the skilled artisan that the starting materials are either commercially available or can be readily prepared by known techniques from commercially available starting materials. All other reactants used to prepare the compounds in the instant invention are commercially available.

The following examples further illustrate the preparation of the compounds of this invention. The examples are illustrative only and are not intended to limit the scope of the invention in any way.

The following abreviations are used in Examples 1 to 7.

$K_2CO_3$ is potassium carbonate
CuO is copper(II) oxide
EtOAc is ethyl acetate
HCl is hydrochloric acid
$NaHCO_3$ is sodium bicarbonate
$MgSO_4$ is magnesium sulfate
KOH is potassium hydroxide
$Na_2SO_4$ is sodium sulfate
DMF is dimethylformamide
$CH_2Cl_2$ is methylene chloride
$NH_3$ is ammonia
HOAc is acetic acid
HBr is hydrogen bromide
NaCN is sodium cyanide
DMSO is dimethylsulfoxide
$H_2O_2$ is hydrogen peroxide
DAP is diammonium phosphate
$AlC_3$ is aluminum chloride
$CHCl_3$ is chloroform

EXAMPLE 1

4-(4-fluorophenoxy)phenylacetamide

A. Preparation of methyl 4-(4-fluorophenoxy)phenylacetate

Into 100 mL of dry pyridine was added, 26.6 g (116 mmole) of methyl (4-bromophenyl)acetate, 13.0 g (116 mmole) of 4-hydroxyphenol, and 32.0 g (232 mmole) of $K_2CO_3$. After providing an argon atmosphere, the reaction mixture was heated with vigorous mechanical stirring until a temperature of 90° C. was reached. At this temperature, 23.2 g of powdered CuO (290 mmole) was added, and then the reaction was heated at reflux for 24 hours. The reaction was cooled and filtered, and evaporated under vacuum. The product was dissolved in EtOAc and washed with cold dilute HCl and cold saturated $NaHCO_3$ solution. After drying over $MgSO_4$ and concentrating under vacuum, the product was purified over silica gel (0 to 30% EtOAc in hexane), giving 9.0 g (30%) of methyl 4-(4-fluorophenoxy)phenylacetate as an oil, which was used without further purification.

$H^1$ NMR ($CDCl_3$) δ: 3.620 (s, 2H), 3.723 (s, 3H), 6.937 (d, 2H), 6.92–7.08 (m, 4H), 7.249 (d, 2H).

B. Preparation of 4-(4-fluorophenoxy)phenylacetic acid

Into 45 mL of diethylene glycol was added, 3.5 g (13.5 mmole) of the phenylacetate prepared above and 5 g of KOH in 15 mL of water. The reaction mixture was heated at 110° C. for 24 hours under nitrogen. The reaction was cooled, acidified with cold concentrated HCl, and extracted between EtOAc and brine three times. The organic layer was shaken with aqueous $K_2CO_3$, and the basic aqueous solution was acidified with dilute HCl and extracted with EtOAc. The solution was dried over $Na_2SO_4$ and concentrated under vacuum, giving 2.78 g (84%) of crystalline 4-(4-fluorophenoxy)phenylacetic acid with a mp of 87–89° C.

Elemental Analysis For $C_{14} H_{11} O_3$ F: Calculated: C, 68.29: H, 4.50; F, 7.72; Found: C, 68.08; H, 4.56; F, 7.99.

C. Preparation of 4-(4-fluorophenoxy)phenyacetamide

Into 50 mL of $CH_2Cl_2$ was dissolved 1.0 g (4.1 mmole) of the phenylacetic acid prepared above, and after adding a few drops DMF, the solution was cooled by an ice bath. To the stirred solution was added 0.46 mL (4.8 mmole) of oxalyl chloride. After 30 minutes, the ice bath was removed and the reaction was allowed to continue for 30 minutes. The solvent was removed under vacuum in a water bath at 40° C. The product was redissolved in dry toluene and the solution was evaporated under vacuum. The product was dissolved in 50 mL of $CH_2Cl_2$ and, while cooling with an ice bath, gaseous $NH_3$ was bubbled in for 10 minutes. The reaction was allowed to slowly come to room temperature over 16 hours, was shaken with brine, dilute cold HCl, and cold saturated $K_2CO_3$ solution. The organic layer was dried over $Na_2SO_4$ and concentrated, giving 0.80 g (80%) of crystalline 4-(4-fluorophenoxy)phenyacetamide, melting at 170–71° C.

Mass Spectral Analysis (FD) m/z: 245 ($M^+$) $H^1$ NMR ($CDCl_3$) δ: 3.32 (s, 2H), 5.90 (bd s, 1H), 6.28 (bd s, 1H), 6.73 (d, 2H), 6.76–6.88 (m, 4H), 7.07 (d, 2H)

EXAMPLE 2

4-phenoxyphenylacetamide

A. Preparation of 1-cyanomethyl-4-phenoxybenzene

Into 100 mL of glacial HOAc was dissolved 34 g (0.2 Mole) of diphenyl ether. To the stirred solution was added 6.78 g (0.22 Mole) paraformaldehyde and 40 mL of 31% solution of HBr in HOAc. The reaction was heated 48 hours at 60° C. and then poured into cold water with stirring. The mixture was extracted with EtOAc and the resulting organic layer was washed with water, dried over $Na_2SO_4$, and evaporated under vacuum to give 50 g of crude 1-bromethyl-4-phenoxybenzene as an oil, which was used in the subsequent reaction without additional purification.

To 60 mL of dry DMF was added, with stirring, 10.0 g (38 mmole) of the crude bromomethyl intermediate and 2.05 g (41.8 mmole)of NaCN. The mixture was heated 16 hours at 60° C. then poured into cold dilute HCl. The mixture was extracted with EtOAc and the resulting organic layer was washed twice with dilute cold HCl, dried over $Na_2SO_4$, and evaporated under vacuum. The product was chromatographed over silica gel (10 to 100% EtOAc in hexane), giving 3.8 g (48%) of 1-cyanomethyl-4-phenoxybenzene as an oil.

Mass Spectral Analysis (FD) m/z: 209 ($M^+$) $H^1$ NMR ($CDCl_3$) δ: 3.75 (s, 2H), 7.03 (d, 2H), 7.15 (t, 1H), 7.30 (d, 2H), 7.37 (d, 2H B. Preparation of 4-phenoxyphenylacetamide To 120 mL of DMSO was added with stirring, 8.79 g (42.5 mmole) of the cyanomethyl intermediate prepared above, 8.0 g of $K_2CO_3$ (58 mmole), and 20 mL of 30% $H_2O_2$. After 1 hour, the reaction mixture was diluted with 150 mL of water, giving crystals of 4-phenoxyphenylacetamide, which weighed 8.7 g (100%) after drying under vacuum and melted at 161–3° C.

Elemental Analysis For $C_{14} H_{13} NO_2$: Calculated: C, 73.99; H, 5.77; N, 6.16: Found: C, 74.07; H, 5.76; N, 5.95. Mass Spectral Analysis (FD) m/z: 227 ($M^+$) $H^1$ NMR ($CDCl_3$) δ: 1.73 (br S, 1H), 3.67 (s, 2H), 7.05 (m, 4H), 7.23 (t, 1H), 7.35(d, 2H), 7.48 (t, 2H)

EXAMPLE 3

3-phenoxyphenylacetamide

3-Phenoxyphenylacetonitrile (1.0 g; 4.8 mmol) was dissolved in DMSO (3 mL) and cooled in an ice-water bath.

Potassium carbonate (0.2 g; 1.5 mmol) was added, followed by dropwise addition of 1.0 mL of 30% hydrogen peroxide. The bath was removed, and the mixture allowed to warm to room temperature while stirring for 40 min. Water was added, and the product isolated as a white crystalline solid by filtration, and washed with fresh water. mp 115–117° C.

Elemental Analysis for $C_{14}$ $H_{13}$ $NO_2$: Calculated: C 73.99, H 5.77, N 6.16; Foind: C 74.01, H 5.51, N 6.20. m/z: 227 (M$^+$).

EXAMPLES 4 and 5

4-benzylphenylacetamide and 3-benzylphenylacetamide

A. Preparation of 4-benzyl-1-cyanomethylbenzene and 3-benzyl-l-cyanomethylbenzene Bromomethylation of diphenylmethane (0.2 Mole) was performed as described in Example 2, above, using paraformaldehyde in HOAC, giving a mixture of 4-benzyl-1-bromomethylbenzene (major product) and 3-benzyl-l-bromomethylbenzene (minor product), which were used in subsequent reactions without further purification.

The crude bromomethylbenzene intermediate (19.6 g, 75 mmole) was treated with NaCN as in Example 2 and, after chromatography over silica gel (10 to 100% EtOAc in hexane), 5.2 g (33%) of 4-benzyl-l-cyanomethylbenzene and 1.43 g (9.2%) of 3-benzyl-1-cyanomethylbenzene were obtained, both as oils.

4-benzyl-l-cyanomethylbenzene

Elemental Analysis For $C_{15}$ $H_{13}$ N: Calculated: C, 86.92; H, 6.32; N, 6.76; Found: C, 87.21; H, 6.40; N, 6.83.3 Mass Spectral Analysis (FD) m/z: 207 (M$^+$).

3-benzyl-1-cyanomethylbenzene

Elemental Analysis For $C_{15}S$ $H_{13}$ N: Calculated: C, 86.92; H, 6.32; N, 6.76; Found: C, 87.20; H, 6.40; N, 6.87.

B. Preparation of 4-benzylphenylacetamide and 3-benzylphenylacetamide

The two cyanomethyl intermediates, prepared above, were converted via the H202 conditions of Example 2 to their corresponding crystalline amides: 4-benzylphenylacetamide (93%), melting at 183–84° C. and 3-benzylphenylacetamide (59%), melting at 136–37° C.

3-Benzylphenylacetamide

Elemental Analysis For $C_{15}$ $H_{15}$ N O: Calculated: C, 79.97; H, 6.71; N, 6.22; Found: C, 79.82; H, 6.65; N, 5.90. Mass Spectral Analysis (FD) m/z: 225 (M$^+$) H$^1$ NMR (CDCl$_3$) 6: 3.57 (s, 2H), 4.04 (s, 2H), 5.12 (br s, 1H), 5.20 (br s, 1H), 7.1–7.4 (m, 9H)

4-Benzylphenylacetamide

H$^1$ NMR (CDCl$_3$) δ: 3.57 (s, 2H), 3.98 (s, H), 7.2–7.3 (m. 9H)

EXAMPLE 6

Sodium 2-(4-carboxybutoxy)-4-(3-phenylphenoxy)phenylacetamide

A. Preparation of 3-(2-phenylphenoxy)anisole

Into 200 mL of pyridine was added 26.7 g (215 mmoles) of 3-methoxyphenol, 50.0 g (215 mmoles) of 1-bromo-2-phenylbenzene, and 59.3 g (430 mmoles) of $K_2CO_3$. Under argon, the mixture was heated to 70° C., and 43.0 g (538 mmoles) powdered CuO was added. The mixture was then heated for 72 hours at reflux with vigorous stirring. After cooling and filtering, the reaction mixture was evaporated under vacuum. The residue was extracted between EtOAC and cold dilute HCl 3 times. The organic layer was dried over $Na_2SO_4$, filtered and evaporated under vacuum. The product was purified via silica gel flash chromatography (0 to 50% EtOAc in hexane), giving 50.9 g (86%) of 3-(2-phenyl)phenoxyanisole as a rystalline solid, melting at 52–54° C.

Elemental Analysis for $C_{19}$ $H_{16}$ $O_2$: Calculated: C, 82.58; H, 5.84; O, 11.58: Found: C, 82.75; H, 5.88; O, 11.40.

B. Preparation of 3-(2-phenylphenoxy)phenol

To 200 mL HOAc and 80 mL of 40% HBr was added 20 g (72.5 mmoles) of the intermediate anisole prepared above. The mixture was heated 6 hours at reflux. Most of the solvent was removed under vacuum, and the residue was shaken between EtOAc and water. The organic layer was washed with saturated $NaHCO_3$, dried over $Na_2SO_4$, and evaporated under vacuum to give 16 g (85%) of 3-(2-phenyl)phenoxyphenol as an oil, which was used without further purification.

Mass Spectral Analysis (FD) m/z: 262 (M$^+$)

C. Preparation of 2-hydroxy-4-(2-phenylphenoxy)phenylglyoxamide

To 50 mL of CHCl3 was added 2.62 g (10 mmoles) of the intermediate phenol, 100 mg DAP, and 2.1 mL (22 mmoles) oxayl chloride. The mixture was heated at reflux for 16 hours. The solvent was removed under vacuum, giving the oxayl chloride condensation product as an oil, which was used without further purification.

The oxayl chloride condensation product (approx.10 mmole) was dissolved in 25 ml of 1,2-dichloroethane and added over 5 min to 3.99 g (30 mmoles) $AlCl_3$ dispersed in 25 mL 1,2-dichloroethane cooled in an ice bath. After 2 hours, the ice bath was removed, and the reaction was allowed to continue for 1 hour. The reaction was placed in an ice bath, and 50 mL concentrated $NH_4OH$ was added to it with vigorous stirring. After 1 hour, the reaction was diluted with water and filtered. The filtrate was diluted further with $CH_2CL_2$ and was shaken in a separatory funnel. The organic layer was washed with cold dilute HCL, dried ver $Na_2SO_4$, and evaporated under vaccum. The product was urified over silica gel (first, a 0–100% EtOAc in hexane gradient, followed by a 20–80% MeOH in EtOAc), giving 206 mg (7.8%) 2-hydroxy-4-(2-phenyl)phenoxyphen-1-yl-glyoxamide. A crystalline analytical sample from $CH_2Cl2$ melted at 100–103° C.

Elemental Analysis For $C_{20}$ $H_{15}$ N $O_4$: Calculated: C, 72.06; H, 4.54; N, 4.20; Found: C, 72.26; H, 4.64; N, 3.94. Mass spectral Analysis (FD) m/z: 333 (M$^+$)

Also obtained in the latter fractions of the above mentioned chromatography was 1.14 g (34%) of 2-hydroxy-4-(2-phenyl)phenoxyphen-1-yl-glyoxylic acid as a crystalline solid, melting at 205° C. (d).

Mass Spectral Analysis (FD) m/z: 334 (M$^+$)

The glyoxylic acid was converted to the more desired glyoxamide as follows: To 25 mL of $CH_2Cl_2$ was dissolved 0.8 g (2.4 mmole) of the intermediate glyoxylic acid. The mixture was cooled by an ice bath, and then a catalytic amount of DMF was added, followed by 0.28 mL (2.9 mmole) of oxayl chloride. After 1 hour, the ice bath was rermoved, and the reaction was allowed to warm to room temperature for 1 hour. The solvent was removed under vacuum, and the product was redissolved in 50 mL of $CH_2Cl_2$. From a lecture bottle, $NH_3$ was bubbled in over a 5 minute period with stirring. The reaction was shaken with cold dilute HCl, and the organic layer was dried over $Na_2SO_4$, and evaporated under vacuum. The crude product crystalized from $CH_2Cl_2$-hexane, giving an additonal 303 mg (38%) of 2-hydroxy-4-(2-phenyl)phenoxyphenylglyoxamide. (17%), mp=100–103° C.

Mass Spectral Analysis (FD) m/z: 333 (M$^+$)

D. Preparation of 2-(4-carboxymethoxybut-lyloxy)-4-(2-phenyl)phenoxyphenylglyoxamide To 62.4 mg (1.3 mmole) of 50% NaH in mineral oil, which had been washed with hexane, was added 50 mL of dry DMF, 0.40 g (1.2 mmole) of 2-hydroxy-4-(2-henyl) phenoxyphenylglyoxamide prepared above, and 100 mg of powdered dry KI and 4-methyl bromobutanate. The reaction mixture was stirred and heated 16 hours at 60° C., quenched with dilute cold HCl, and after diluting further with cold brine, it was extracted with EtOAc. The organic layer was washed with acidified brine twice, dried over $Na_2SO_4$, evaporated under vacuum. When chromatographed over silica gel (20 to 80% EtOAc in hexane), 254 mg (47%) 2-(4-carbomethoxy)butoxy-4-(2-phenyl) phenoxyphenylglyoxamide was prepared as an oil.

$H^1$ NMR ($CDCl_3$) δ: 1.7–1.9 (m, 4H), 2.39 (t, 2H), 3.69 (s, 3H), 3.93 (t, 2H), 5.84 (br s, 1H), 6.29 (br s, 1H), 6.46 (s, 1H), 6.49 (d, 1H), 7.12 (d, 1H), 7.3–7.5 (m, 8H), 7.65 (d, 1H); Mass Spectral Analysis (FD) m/z: 447 ($M^+$).

E. Preparation of 2-(4-carbomethoxybutoxy)-4-(2-phenylphenoxy)phenyl-2-hydroxyacetamide Into 25 mL of MeOH was dissolved 358 mg (0.8 mmole) of 2-(4-carbomethoxy)butoxy-4-(2-phenylphenoxy) phenylglyoxamide, and after cooling with an ice bath, 38 mg (1.0 mmole) of $NaBH_4$. After 1 hour most of the solvent was removed under vacuum, and the residue was extracted between EtOAc and dilute HCl. The organic layer was dried over $Na_2SO_4$ and evaporated under vacuum to provide 2-(4-carbomethoxybutoxy)-4-(2-phenylphenoxy)phenyl-2-hydroxyacetamide as an oil, which was used in the susequent reaction without further purification.

F. Preparation of 2-(4-carbomethoxybutoxy)-4-(2-phenylphenoxy)phenylacetamide

The 2-hydroxyacetamide intermediate (approx 0.8 mmole), prprared above, was dissolved in 15 mL $CH_2Cl_2$, and 0.5 mL $Et_3SiH$ and 1 mL TFA was added at room temperature. The mixture was stirred for 4 hours and then poured into saturated $NaHCO_3$. The organic layer was separated, washed with brine, dried over $MgSO_4$, and concentrated. The product was purified over a preparative silica gel plate (80% EtOAc-20% Hexane elution), giving 7.3 mg (2%) of 2-(4-carbomethoxybutoxy)-4-(2-phenylphenoxy) phenylacetamide as an oil.

$H^1$ NMR ($CDCl_3$) d: 1.7–1.9 (m, 4H), 2.40 (t, 2H), 3.50 (s, 2H), 3.69 (s,3H), 3.91 (t, 2H), 5.22 (br s, 1H), 5.82 (br s, 1H), 6.46(d, 1H), 6.50 (s, 1H), 7.05 (d, 1H), 7.12 (d, 1H), 7.2–7.6 (m, 8H)

G. Preparation of sodium 2-(4-carboxybutoxy)-4-(2-phenylphenoxy)phenylacetamide

The intermediate acetamide (7.3 g, 0.01 mmole), prepared above, was dissolved in 10 mL of MeOH and treated with 0.84 mL (0.017 mmole) of 0.2 N NaOH for 16 hours at room temperature. Solvent was removed under vacuum, giving approximately 6 mg of sodium 2-(4-carboxybutoxy)-4-(2-phenylphenoxy)phenylacetamide as an amorphous solid.

$H^1$ NMR ($CH_3OH$-$d_4$) d:1.6–1.9 (m, 4H), 2.20 (t, 2H), 3.32 (s, 2H). 3.87 (t, 2H), 6.35 (d, 1H), 6.50 (s, 1H), 7.03 (d, 2H), 7.2–7.6 (m, 8H)

EXAMPLE 7

Sodium(RS)-2-(4-carboxybutoxy)-4-(3-phenylphenoxy)phenyl-2-hydroxyacetamide

E. Preparation of (RS)-2-(4-carbomethoxybutoxy)-4-(3-phenylphenoxy)-2-hydroxyacetamide The intermediate, 2-(4-carbomethoxybutoxy)-4-(3-phenylphenoxy)phenylglyoxamide (0.532 g, 1.19 mmole), prepared as described in Example 6, steps A–D, above was treated with 45 mg (1.43 mmole) of $NaBH_4$ in 35 mL of MeOH as described in Example 6, step E to give, after purification of crude product over silica gel (0–100% EtOAc in hexane, followed by 20% MeOH in EtOAc), 125 mg (23%) of (RS)-2-(4-carbomethoxybutoxy)-4-(3-phenylphenoxy)-2-hydroxyacetamide. Crystals from $CH_2Cl_2$-hexane melted at 122–3° C.

Elemental Analysis For $C_{26}H_{27}N O_6$: Calculated: C, 69.47; H, 6.05; N, 3.12; Found: C, 69.31; H, 6.18; N, 3.12. $H_1$ NMR (CDC13) δ: 1.7–2.0 (m, 4H), 2.40 (t, 2H), 3.69 (s, 3H), 3.99 (t, 2H), 5.87 (s, 1H), 6.34 (s, 1H), 6.60 (s, 1H), 6.63 (d, 1H), 7.07 (m, 1H), 7.33 (s, 1H), 7.35–7.43 (m, 2H), 7.43–7.50 (m, 5H), 7.58 (d, 2H), 7.75 (d, 1H) Mass Spectrum Analysis (FD) m/z: 449 ($M^+$)

F. Preparation of sodium (RS)-2-(4-carboxybutoxy)-4-(3-phenylphenoxy)phenyl-2-hydroxyacetamide The intermediate 2-hydroxyacetamide, prepared above, (45 mg, 0.1 mmole) was dissolved in 10 mL of MeOH and treated with 0.5 mL (0.1 mmole) of 0.2 N NaOH for 16 hours at room temperature. Solvent was removed under vacuum to give sodium (RS)-2-(4-carboxybutoxy)-4-(3-phenylphenoxy)phenyl-2-hydroxyacetamide as a crystalline solid, melting at 147° C. (d).

Titration (66% DMF): pK=7.4, Apparent Mol. Wt.=463 (457 Calculated) Mass Spectral Analysis (FAB) m/z: 458 [$(M+1)^+$]

Therapeutic Use of Phenyl Acetamide Compounds

The phenyl acetamide compounds described herein are believed to achieve their beneficial therapeutic action principally by direct inhibition of human $sPLA_2$, and not by acting as antagonists for arachidonic acid, nor other active agents below arachidonic acid in the arachidonic acid cascade, such as 5-lipoxygenases, cyclooxygenases, and etc.

The method of the invention for inhibiting $sPLA_2$ mediated release of fatty acids comprises contacting $sPLA_2$ with an therapeutically effective amount of the compound of Formula (II), its salt or a prodrug derivative thereof.

The compounds of the invention may be used in a method of treating a mammal (e.g., a human) to alleviate the pathological effects of septic shock, adult respiratory distress syndrome, pancreatitus, trauma, bronchial asthma, allergic rhinitis, and rheumatoid arthritis; wherein the method comprises administering to the mammal a compound of formula (II) in a therapeutically effective amount. A "therapeutically effective" amount is an amount sufficient to inhibit $sPLA_2$ mediated release of fatty acid and to thereby inhibit or prevent the arachidonic acid cascade and its deleterious products. The therapeutic amount of compound of the invention needed to inhibit $sPLA_2$ may be readily determined by taking a sample of body fluid and assaying it for $sPLA_2$ content by conventional methods.

Pharmaceutical Formulations of the Invention

As previously noted the compounds of this invention are useful for inhibiting $sPLA_2$ mediated release of fatty acids such as arachidonic acid. By the term, "inhibiting" is meant the prevention or therapeutically significant reduction in release of $sPLA_2$ initiated fatty acids by the compounds of the invention. By "pharmaceutically acceptable" it is meant the carrier, diluent or excipient must be compatible with the other ingredients of the formulation and not deleterious to the recipient thereof.

In general, the compounds of the invention are most desirably administered at a concentration that will generally afford effective results without causing any serious side effects and can be administered either as a single unit dose, or if desired, the dosage may be divided into convenient subunits administered at suitable times throughout the day.

The specific dose of a compound administered according to this invention to obtain therapeutic or prophylactic effects will, of course, be determined by the particular circumstances surrounding the case, including, for example, the route of administration the age, weight and response of the individual patient, the condition being treated and the severity of the patient's symptoms. Typical daily doses will contain a non-toxic dosage level of from about 0.01 mg/kg to about 50 mg/kg of body weight of an active compound of this invention.

Preferably the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

A "chronic" condition means a deteriorating condition of slow progress and long continuance. As such, it is treated when it is diagnosed and continued throughout the course of the disease. An "acute" condition is an exacerbation of short course followed by a period of remission. In an acute event, compound is administered at the onset of symptoms and discontinued when the symptoms disappear.

Pancreatitis, trauma-induced shock, bronchial asthma, allergic rhinitis and rheumatoid arthritis may occur as an acute event or a chronic event. Thus, the treatment of these conditions contemplates both acute and chronic forms. Septic shock and adult respiratory distress, on the other hand, are acute conditions treated when diagnosed.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the phenyl acetamide compounds of the invention together with a pharmaceutically acceptable carrier or diluent therefor. The present pharmaceutical formulations are prepared by known procedures using well known and readily available ingredients.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from about 1 to about 99 weight percent of the active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol. Other compositions can be made by dispersing the finely divided active ingredient in aqueous starch or sodium carboxymethyl cellulose solution or in a suitable oil.

The following pharmaceutical formulations 1 through 8 are illustrative only and are not intended to limit the scope of the invention in any way. "Active ingredient", refers to a compound according to Formula (I) or a pharmaceutically acceptable salt, solvate, or prodrug thereof.

Formulation 1

Hard gelatin capsules are prepared using the following ingredients:

|  | Quantity (mg/capsule) |
| --- | --- |
| 4-(3,5-diphenylphenoxy)-5-bromophenylacetamide | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| 3-(4-(3,5-di(4-fluorophenyl)))benzyl-6-butylphenylacetamide | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
|---|---|
| 3-(5-bromo)benzyl-5-ethylphenylacetamide | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| | |
|---|---|
| 2-[2-(2-carboxyethoxy)-4-(2,6-dichlorophenoxy)]phenyl-2-hydroxyacetamide | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| | |
|---|---|
| 2-(2-phosophonyl)ethoxy-4-(4-propoxyphenoxy)-6-isopropylphenyl-2-hydroxyacetamide | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| | |
|---|---|
| 2-((3-propoxycarbonyl)prop-1-yloxy)-4-(4-(4-chlorophenyl)benzyl)phenyl-2-hydroxyacetamide | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| | |
|---|---|
| 2-(7-methoxysulfonyl)hept-1-yloxy)-4-((2-fluoro-6-phenyl)benzyl)phenyl-2-hydroxyacetamide | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| 2-(8-methoxycarbonyl)oct-1-yloxy)-4-(3-bromo-5-methylbenzyl)-5-propylphenylacetamide | 100 mg |
| Isotonic saline | 1,000 ml |

The solution of the above ingredients generally is administered intravenously to a subject at a rate of 1 ml per minute.

ASSAY EXPERIMENTS

Assay Example 1

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A. Dennis, *Analyti-* cal Biochemistry, 204, pp. 190–197, 1992 (the disclosure of which is incorporated herein by reference):

Reagents:
  REACTION BUFFER
    $CaCl_2 \cdot 2H_2O$ (1.47 g/L)
    KCl (7.455 g/L)
    Bovine Serum Albumin (fatty acid free) (1 g/L) (Sigma A-7030, product of Sigma Chemical Co. St. Louis Mo., USA)
    TRIS HCl (3.94 g/L)
    pH 7.5 (adjust with NaOH)
  ENZYME BUFFER
    0.05 $NaOAc \cdot 3H_2O$, pH 4.5
    0.2 NaCl
    Adjust pH to 4.5 with acetic acid
  DTNB—5,5'-dithiobis-2-nitrobenzoic acid
  RACEMIC DIHEPTANOYL THIO—PC
    racemic 1,2-bis(heptanoylthio)-1, 2-dideoxy-sn-glycero-3-phosphorylcholine
    TRITON X-100™ prepare at 6.249 mg/ml in reaction buffer to equal 10uM.
    TRITON X-100™ is a polyoxyethylene non-ionic detergent-manufactured by Pierce Chemical Company, 3747 N. Meridian Road, Rockford, Ill. 61101.
  REACTION MIXTURE
    A measured volume of racemic dipheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains lmM diheptanoly thio-PC substrate, 0.29 mm Triton X-100™ detergent, and 0.12 mm DTMB in a buffered aqueous solution at pH 7.5.

Assay Procedure:
  1. Add 0.2 ml reaction mixture to all wells;
  2. Add 10 ul test compound (or solvent blank) to appropriate wells, mix 20 seconds;
  3. Add 50 nanograms of $sPLA_2$ (10 microliters) to appropriate wells;
  4. Incubate plate at 40° C. for 30 minutes;
  5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, $IC_{50}$ values were determined. Typically, the $IC_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ were determined by plotting log concentration versus inhibition values in the range from 10–90% inhibition.

Compounds of the instant invention were tested in Assay Example 1 and were found to be effective at concentrations of less than 78 µM.

Assay Example 2

Method:
Male Hartley strain guinea pigs (500–700g) were killed by cervical dislocation and their heart and lungs removed intact and placed in aerated (95% $O_2$:5% $CO_2$) Krebs buffer. Dorsal pleural strips (4×1×25 mm) were dissected from intact parenchymal segments (8×4×25 mm) cut parallel to the outer edge of the lower lung lobes. Two adjacent pleural strips, obtained from a single lobe and representing a single tissue sample, were tied at either end and independently attached to a metal support rod. One rod was attached to a Grass force-displacement transducer Model FTO3C, product of Grass Medical Instruments Co., Quincy, Mass., USA). Changes in isometric tension were displayed on a monitor and thermal recorder (product of Modular Instruments, Malvern, Pa.). All tissues were placed in 10 ml jacketed tissue baths maintained at 37° C. The tissue baths were continuously aerated and contained a modified Krebs solution of the following composition (millimolar) NaCl, 118.2; KCl, 4.6; $CaCl_2 \cdot 2H_2O$, 2.5; $MgSO_4 \cdot 7H_2O$, 1.2; $NaHCO_3$, 24.8; $KH_2PO_4$, 1.0; and dextrose, 10.0. Pleural strips from the opposite lobes of the lung were used for paired experiments. Preliminary data generated from tension/response curves demonstrated that resting tension of 800 mg was optimal. The tissues were allowed to equilibrate for 45 min. as the bath fluid was changed periodically.

Cumulative concentration-response curves:
Initially tissues were challenged 3 times with KCl (40 mM) to test tissue viability and to obtain a consistent response. After recording the maximal response to KCl, the tissues were washed and allowed to return to baseline before the next challenge. Cumulative concentration-response curves were obtained from pleural strips by increasing the agonist concentration ($sPLA_2$) in the tissue bath by half-$log_{10}$ increments while the previous concentration remained in contact with the tissues (Ref.1, supra.). Agonist concentration was increased after reaching the plateau of the contraction elicited by the preceding concentration. One concentration-response curve was obtained from each tissue. To minimize variability between tissues obtained from different animals, contractile responses were expressed as a percentage of the maximal response obtained with the final KCl challenge. When studying the effects of various drugs on the contractile effects of $sPLA_2$, the compounds and their respective vehicles were added to the tissues 30 minutes prior to starting the $sPLA_2$ concentration-response curves.

Statistical Analysis:
Data from different experiments were pooled and presented as a percentage of the maximal KCl responses (mean±S.E.). To estimate the drug induced rightward shifts in the concentration response curves, the curves were analyzed simultaneously using statistical nonlinear modeling methods similar to those described by Waud (1976), Equation 26, p. 163, (Ref.2). The model includes four parameters: the maximum tissue response which was assumed the same for each curve, the $ED_{50}$ for the control curve, the steepness of the curves, and the $pA_2$, the concentration of antagonist that requires a two-fold increase in agonist to achieve an equivalent response. The Schild slope was determined to be 1, using statistical nonlinear modeling methods similar to those described by Waud (1976), Equation 27, p. 164 (Ref. 2). The Schild slope equal to 1 indicates the model is consistent with the assumptions of a competitive antagonist; therefore, the $pA_2$ may be interpreted as the apparent $K_B$, the dissociation constant of the inhibitor.

To estimate the drug-induced suppression of the maximal responses, $SPLA_2$ responses (10 µg/ml) were determined in the absence and presence of drug, and percent suppression was calculated for each pair of tissues. Representative examples of inhibitory activities are presented in Table 2, below.

Ref. 1—van, J.M.: Cumulative dose-response curves. II. Technique for the making of dose-response curves in isolated organs and the evaluation of drug parameters. *Arch. Int. Pharmacodyn. Ther.*, 143: 299–330, 1963.

Ref. 2—Waud, D.: Analysis of dose-response relationships. in *Advances in General and Cellular Pharmacology* eds Narahashi, Bianchi 1:145–178, 1976.

Compounds of the instant invention were tested in Assay Example 2 and were found to be effective at concentrations below 100 µg.

While the present invention has been illustrated above by certain specific embodiments, it is not intended that these specific examples should limit the scope of the invention as described in the appended claims.

What is claimed is:

1. A compound of the formula (I)

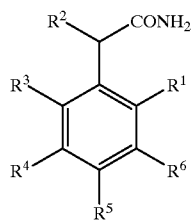

(I)

wherein:
$R^1$ is —O $(CH_2)_n Z$,
$R^2$ is —H or —OH;
$R^3$ and $R^4$ are each independently —H, halo or —($C_{1-C4}$) alkyl;
One of $R^5$ and $R^6$ is —$YR^7$ and the other is —H, where Y is —O— or —$CH_2$— and $R^7$ is phenyl or phenyl substituted with one or two substituents selected from the group consisting of halo, —($C_1$–$C_4$)alkyl, ($C_1$–$C_4$) alkoxy, phenyl or phenyl substituted with one or two halo groups;
Z is —$CO_2R$, —$PO_3R_2$ or —$SO_3R$ where R is —H or —($C_1$–$C_4$)alkyl; and
n is 1–8;
or a pharmaceutically acceptable salt, racemate or optical isomer thereof;
provided that when $R^1$ and $R^4$ are hydrogen and $R^6$ is $YR_7$, where Y is $CH_2$, $R^7$ cannot be phenyl substituted with methoxy or chloro groups; and when $R^1$, $R^2$, $R^3$, $R^4$ and $R^6$ are hydrogen and $R^5$ is $YR^7$ where Y is —O—, $R^7$ cannot be phenyl; and when $R^1$, $R^2$, $R^3$, $R^4$ and $R^6$ are hydrogen, $R^5$ is $YR^7$ where Y is $CH_2$, $R^7$ cannot be phenyl substituted with methoxy or chloro groups.

2. A compound of formula I as claimed in claim 1 wherein $R^2$, $R^3$ and $R^4$ is H, Y is oxygen or $CH_2$, $R^7$ is phenyl or phenyl substituted at the meta position with one or two substituents selected from —($C_1$–$C_4$)alkyl, ($C_1$–$C_4$)alkoxy, and phenyl, and n is 4–5.

3. A pharmaceutical formulation comprising a compound of formula I as claimed in claim 1 together with a pharmaceutically acceptable carrier or diluent therefor.

4. A compound which is 2-(4-carboxybutoxy)-4 -(3-phenylphenoxy) phenylacetamide.

5. A method of selectively inhibiting $sPLA_2$ in a mammal in need of such treatment comprising administering to said mammal a pharmaceutically effective amount of a compound of formula I as claimed in claim 1.

6. A method of claim 5 wherein the mammal is a human.

7. A method of claim 5 wherein $R^2$, $R^3$ and $R^4$ is H, Y is oxygen or $CH_2$, $R^7$ is phenyl or phenyl substituted at the meta position with one or two substituent selected from halo, —($C_1$–$C_4$)alkyl, ($C_1$–$C_4$)alkoxy, phenyl or phenyl substituted with halo and n is 4–5.

8. A method of claim 5 wherein the compound is 2-(4-carboxybutoxy)-4-(3-phenylphenoxy) phenylacetamide.

9. A method of claim 5 of alleviating the pathological effects of septic shock, adult respiratory distress syndrome, pancreatitis, trauma-induced shock, bronchial asthma, allergic rhinitis, and rheumatoid arthritis which comprises administering to a mammal in need of such treatment a compound of formula I in an amount sufficient to inhibit $sPLA_2$ mediated release of fatty acid and to thereby inhibit or prevent the arachidonic acid cascade and its deleterious products.

10. A method of claim 9 wherein the mammal is a human.

11. A method of claim 9 wherein $R^2$, $R^3$ and $R^4$ is H; Y is oxygen or $CH_2$, $R^7$ is phenyl or phenyl substituted at the meta position with one or two substituents selected from halo, —($C_1$–$C_4$)alkyl, ($C_1$–$C_4$)alkoxy, phenyl or phenyl substituted with halo and n is 4–5.

12. A method of claim 9 wherein the compound is 2-(4-carboxybutoxy)-4-(3-phenylphenoxy) phenylacetamide.

* * * * *